United States Patent [19]

Newman et al.

[11] 4,147,163
[45] Apr. 3, 1979

[54] MEDICAL INSTRUMENT AND HANDLE ASSEMBLY

[75] Inventors: Richard W. Newman; John D. Connors, both of Auburn, N.Y.

[73] Assignee: Welch Allyn, Inc., Skaneateles Falls, N.Y.

[21] Appl. No.: 831,058

[22] Filed: Sep. 6, 1977

[51] Int. Cl.² .................... A61B 1/22; H01M 10/44; F21L 9/00
[52] U.S. Cl. .......................... 128/9; 320/2; 362/183
[58] Field of Search ............ 128/9; 362/183; 320/2, 320/3, 15

[56] References Cited

U.S. PATENT DOCUMENTS

| Re. 25,388 | 5/1963 | Moore | 320/3 X |
|---|---|---|---|
| 1,999,079 | 4/1935 | Blake | 320/2 X |
| 3,070,748 | 12/1962 | Worobey et al. | 362/183 X |
| 3,071,747 | 1/1963 | Moore | 362/198 X |
| 3,220,888 | 11/1965 | Moore et al. | 362/2 X |
| 3,305,779 | 2/1967 | Errichiello | 320/4 X |
| 3,393,312 | 7/1968 | Dahl | 362/183 X |
| 3,698,387 | 10/1972 | Moore et al. | 128/9 |
| 3,978,850 | 9/1976 | Moore et al. | 128/9 |
| 4,092,580 | 5/1978 | Prinsze | 362/185 X |

FOREIGN PATENT DOCUMENTS 1419828 12/1975 United Kingdom ............... 320/2

*Primary Examiner*—Jerome Schnall
*Attorney, Agent, or Firm*—Bruns & Jenney

[57] ABSTRACT

A battery handle for an electrically illuminated diagnostic instrument, the handle being able to accommodate either non-rechargeable or rechargeable cells. The handle is constructed so that rechargeable cells can be recharged without removing the cells from the handle. Non-rechargeable cells are insulated from the recharging circuit so that if the handle is inadvertently placed in a recharging unit with non-rechargeable cells in it, the latter will not be damaged. The handle includes a neck portion to which different diagnostic instruments can be releasably connected, and with no instruments attached the neck portion can be used as a general illuminator with particular utility as a throat illuminator.

10 Claims, 5 Drawing Figures

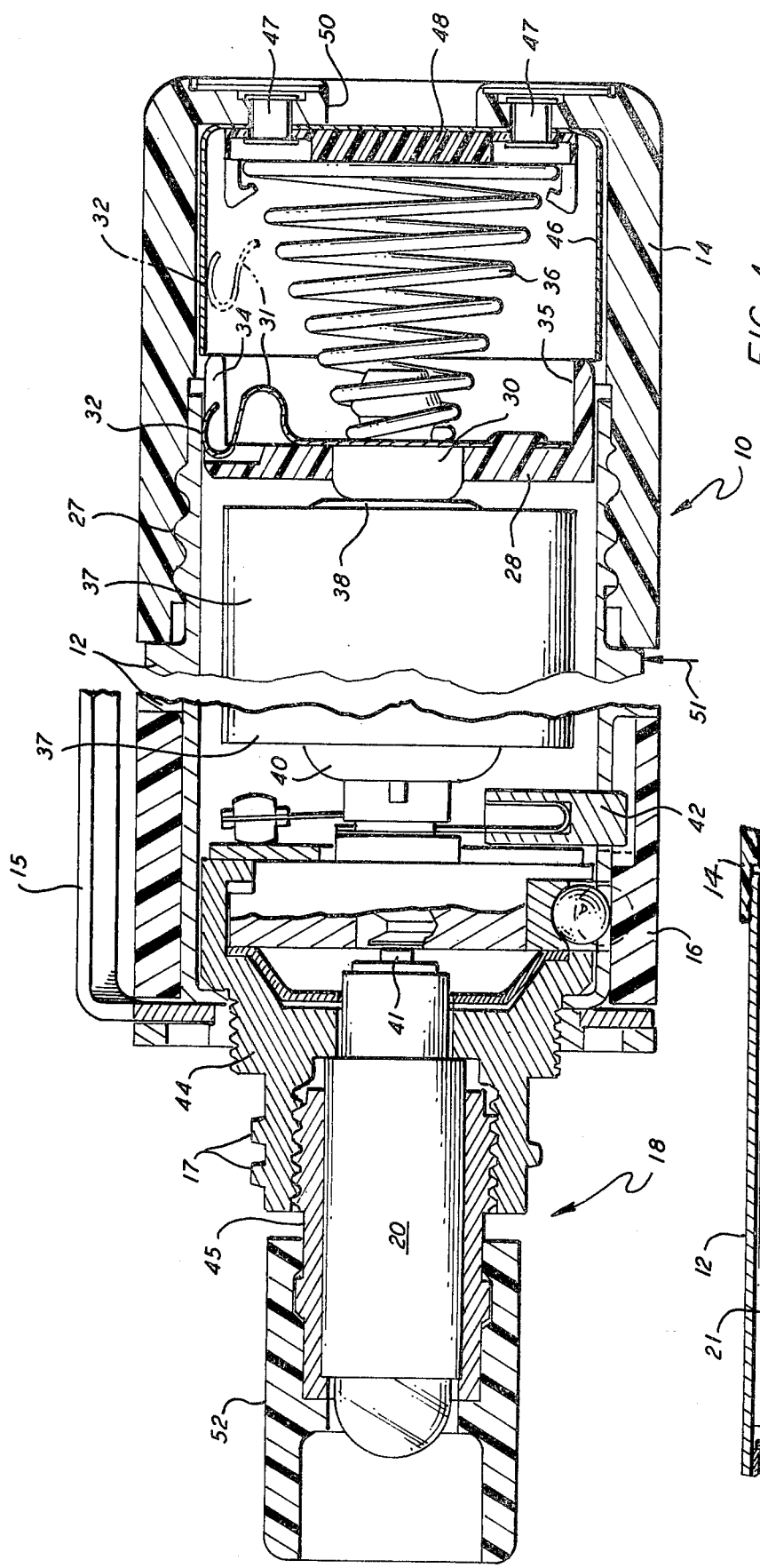

MEDICAL INSTRUMENT AND HANDLE ASSEMBLY

BACKGROUND OF THE INVENTION

This invention relates generally to medical instruments, and has particular reference to a novel battery handle for electrically illuminated diagnostic instruments. More specifically, the handle is adapted to accommodate either non-rechargeable or rechargeable cells.

A battery handle of the type that provides a combined power source and handle for one of several different interchangeable medical instruments has long been known in the art. Such handles have been constructed for use with non-rechargeable or single use cells and also for rechargeable cells but, to the best of the applicant's knowledge, a battery handle capable of accepting either type of cell has not been provided heretofore. Prior art battery handles are disclosed in U.S. Pat. Nos. 3,071,747 and Re. 25,388, both owned by the assignee of the present invention.

Portable radio receivers capable of using either non-rechargeable or rechargeable cells have been provided but the means for enabling this is to be done differs materially from the means utilized by the present invention. The radio receivers referred to are disclosed in U.S. Pat. Nos. 3,070,748 . and 3,305,779, and this is the closest prior art known to applicants.

SUMMARY OF THE INVENTION

The battery handle of the present invention is adapted to receive either a pair of non-rechargeable cells or a pair of rechargeable cells. The latter, however, are assembled in a special pack to be described while the non-rechargeable cells are in no way connected to one another.

The length of the special pack exceeds the overall length of a pair of non-rechargeable cells.

In the interior of the battery handle there is a movable contact that engages a terminal of whichever type of cell is being utilized to the handle. When this contact is engaged by a terminal of a non-rechargeable cell, a circuit is completed to a light source in the handle in a substantially conventional manner. The battery handle also has a recharging circuit that is insulated from the non-rechargeable cell circuit. When rechargeable cells are used they cause the movable contact to move into engagement with a part of the recharging circuit whereby the cells can be recharged when the handle is placed in a recharging unit. When not in a recharging unit, the rechargeable cells form a part of a substantially conventional circuit to the light source.

The light source is located in a neck portion of the battery handle which neck portion is adapted to have one of several different interchangeable medical instruments releasably connected thereto. With no instruments attached to the neck portion, the battery handle can be conveniently used as a general illuminator.

BRIEF DESCRIPTION OF THE DRAWINGS

FIG. 4 is a greatly enlarged, fragmentary longitudinal sectional view of the battery handle, most of the mid-portion thereof being removed; and FIG. 5 is a side elevation of the rechargeable cell assembly or pack, the pack being mounted in the handle which is shown fragmentarily and in section.

DESCRIPTION OF THE PREFERRED EMBODIMENT

Figure 1:
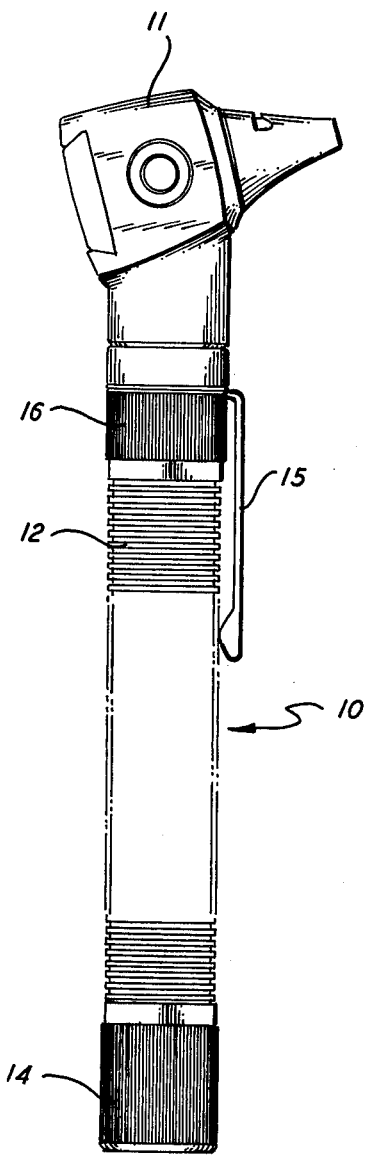
FIG. 1 is a side elevation of a battery handle embodying the invention with an otoscope connected thereto.
Figure 2:
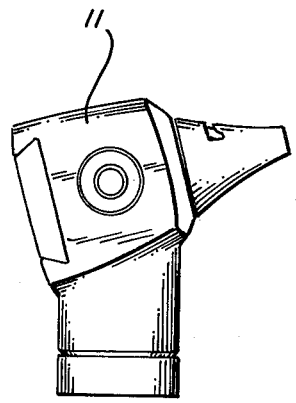
FIG. 2 is a side elevation of the otoscope alone.

Referring now to the drawings, and with particular reference to FIGS. 1-3, 10 generally indicates a battery handle embodying the invention, an otoscope 11 being releasably connected thereto. The handle includes a tubular barrel or main body portion 12, a removable bottom closure 14 and a pocket clip 15. A rotatable ring 16 serves as an on-off switch and also as a rheostat control.

Figure 3:
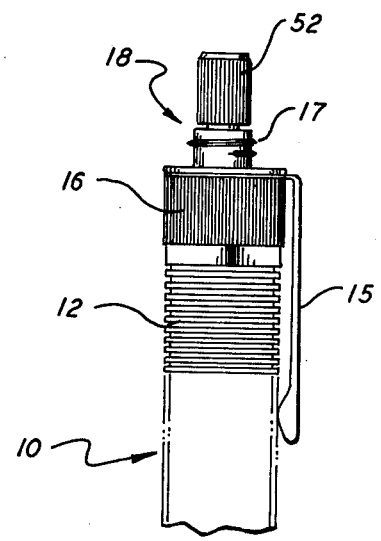
FIG. 3 is a fragmentary side elevation of the battery handle alone.

The otoscope 11 is secured to the battery handle 10 by a quick connect and disconnect thread 17, FIGS. 3 and 4. Other instruments, such as ophthalmoscopes and retinoscopes (not shown), can also be used with the handle. Other means can also be employed to secure the instruments to the handle such as those disclosed in co-pending application Ser. No. 784,931, filed Apr. 5, 1977 by William C. Moore et al. Otoscope 11 is substantially the same as the otoscopes disclosed in U.S. Pat. Nos. 3,698,387 and 3,978,850, both owned by the assignee of the present invention, and therefore reference may be had to those patents for its construction.

In accord with the invention, the handle 10 is adapted to receive either a pair of non-rechargeable cells or a pair of rechargeable cells, and the latter can be recharged without removing them from the handle. The handle, therefore, includes a charging circuit that is insulated at all times from the non-rechargeable cells. At one end, the handle is provided with a neck portion indicated generally at 18, and a lamp 20 is mounted in this neck portion as shown in FIG. 4. The handle can also be used with an instrument having its own light source in which case there will be no lamp in the neck portion 18.

The rechargeable cells are assembled in a special pack 21 the construction of which is disclosed in U.S. Pat. No. 3,220,888, owned by the assignee of the present invention. The pack 21 has a tubular cover 22 of insulating material and this cover has a side aperture 24 through which a negative terminal 25 projects. The pack is arranged so that there is a positive terminal 26 at each of its ends whereby the pack cannot be misoriented in the handle. The rechargeable cell pack 21 is longer than the overall length of a pair of non-rechargeable cells in end to end abutting relation.

At the end of the handle opposite the neck portion 18 the bottom closure 14 is normally threaded onto the main body portion 12 as shown at 27 in FIG. 4. The bottom closure is made of an insulating material such as plastic and the main body is made of a conductive material such as metal. Inside the handle, adjacent this connection, there is a movable contact assembly comprising an inverted, shallow cup member 28 of insulating material, a central metal terminal 30 and a metal spring contact finger 31.

The outer end 32 of contact finger 31 extends through a cut out portion 34 in the side wall 35 of cup member 28 which permits it to contact the main body portion 12 as shown in solid lines in FIG. 4. The central terminal 30 is in metal to metal contact with the finger 31 and at its lower end is engaged by a helical compression spring 36 which operates to bias the movable contact assembly towards the opposite end of the handle.

When non-rechargeable or primary cells 37, FIG. 4, are used in the battery handle, the negative terminal 38 of the lower cell is contacted by the central terminal 30 and the movable contact assembly is positioned in the handle as shown in solid lines. The positive terminal (not shown) of the lower cell contacts the negative terminal (not shown) of the upper cell, and the positive terminal 40 of the latter is connected to the base terminal 41 of the lamp 20 through a known type of rheostat 42. The rheostat is actuated by the previously mentioned external ring 16 to turn the lamp on and off and to control the brightness of the illumination. The circuit for the lamp is completed through the central terminal 30 of the movable contact assembly, contact finger 31, the main body portion 12 of the handle, an upper metal closure 44 for the handle and a metal sleeve 45 that is threaded into the closure and is in contact with the side terminal of the lamp. As will be understood, the polarity of the non-rechargeable cells can be reversed.

When rechargeable cells in a pack 21, FIG. 5, are used in the battery handle, the greater length of the pack causes spring 36 to be further compressed and the movable contact assembly to be moved to the position shown in phantom lines in FIG. 4. In this position, the contact finger 31 has been moved out of engagement with the main body portion 12 and into engagement with the side wall of a metal cup 46 that is secured to the inside of the bottom closure 14 as by rivets 47. The rivets also hold a plastic disc 48 in position at the bottom of cup 46, the disc serving to insulate the spring 36 from the cup. The bottom wall of the bottom closure 14 is provided with a central opening 50 which exposes a portion of the cup bottom for recharging as will be explained.

When the rechargeable cells in pack 21 are not being recharged, the circuit for lamp 20 is basically the same as the circuit for the non-rechargeable cells 37. Thus, the positive terminal 26, FIGS. 4 and 5, at the upper end of the pack makes electrical contact with the base terminal 41 of the lamp through the rheostat 42, and the negative terminal 25 makes electrical contact with the lamp side terminal through the main body portion 12 and the previously mentioned upper closure 44 and sleeve 45.

When the battery handle is placed in a recharging unit (not shown) to recharge the cells in pack 21, the unit will apply a positive charge to the cup 46 through the opening 50 in the bottom closure 14. From the cup, current will be conducted through the contact finger 31 in engagement therewith and central terminal 30 to the positive terminal 26 at the lower end of the pack, FIG. 5. The lamp circuit will at this time be open. The recharging circuit will be completed by a current path between the recharging unit and the main body portion 12 at some point as indicated by the arrow 51, FIGS. 4 and 5, the body portion being in contact with the negative terminal 25 of the cell pack. The body portion 12 is at all times insulated from the cup 46 of the recharging circuit.

If the battery handle 10 contains non-rechargeable cells 37 and is inadvertently placed in a recharging unit, the cells will not be damaged. Thus, with these cells, the movable contact assembly will be in the solid line position of FIG. 4, contact finger 31 will be out of engagement with cup 46 and the recharging circuit will therefore be open. As is well known in the art, any attempt to recharge a non-rechargeable cell can seriously damage the cell and even cause it to explode.

The battery handle of the invention is shown in FIG. 1 in conjunction with an otoscope and it has been noted that other instruments can also be used with it. The handle can also be advantageously used by itself, FIGS. 3 and 4, as a general illuminator and more particularly as a throat illuminator. This is possible because the lamp 20 and lamp controls are positioned in the neck portion 18 of the handle. To insure that the heat of the lamp won't burn or cause discomfort to the patient or physician, the upper portion of the lamp is encircled by a non-metallic shroud 52 of some material such as polypropylene having low heat conductivity.

From the foregoing description it will be apparent that the invention provides a battery handle having a novel construction that makes the handle more versatile than those previously developed. As will be apparent to those familiar with the art, the invention may be embodied in other specific forms without departing from the spirit or essential characteristics thereof.

We claim:

1. A battery handle for a medical diagnostic instrument, the handle being arranged to accommodate either non-rechargeable or rechargeable type cells, a pair of the latter cells being assembled in a pack that is dimensionally different than a pair of the former, a movable contact member engageable with a terminal of whichever type of cell is employed in the handle, means in the handle to complete a circuit between the cells and a light source, said last-named means including means for conducting current from one end of the handle to the other, current conducting means forming a part of the recharging circuit for the rechargeable cells, said last-named means being insulated from the handle current conducting means, the movable contact members when engaging the terminal of a non-rechargeable cell being position so as to contact the handle current conducting means, the movable contact member when engaging the terminal of a rechargeable cell being positioned so as to contact the recharging circuit current conducting means whereby the cell can be recharged.

2. A battery handle as defined in claim 1 wherein the handle includes a light source, and a neck portion to which the head portion of the diagnostic instrument can be releasably secured, the light source being positioned in said neck portion.

3. A battery handle as defined in claim 2 wherein the instrument head portion is secured to the handle neck portion by a threaded connection.

4. A battery handle as defined in claim 2 wherein the light source and neck portion are arranged so that the handle can be effectively used for diagnostic purposes with or without the instrument head portion.

5. A battery handle for a medical diagnostic instrument, the handle being adapted to accommodate either non-rechargeable or rechargeable type cells, a pair of the latter being assembled in a pack having a different length than the overall length of a pair of the former, a movable contact in the handle engageable with a terminal of whichever type cell is employed in the handle, said contact being spring biased into engagement with the terminal, means in the handle to complete a circuit between the cells and a lamp, said last-named means including means for conducting current from a point in the handle adjacent the movable contact to one terminal of the lamp, a current conducting member forming a part of the recharging circuit for the recharging cells, said last-named member being adjacent the movable contact and insulated from the means for conducting current to said one lamp terminal, the movable contact when engaging the terminal of a non-rechargeable cell being positioned so as to contact the means for conducting current to said one lamp terminal, the movable contact when engaging the terminal of a rechargeable cell being positioned so as to contact the conducting member of the recharging circuit whereby the cell can be recharged.

6. A battery handle as defined in claim 5 wherein a portion of the conducting member of the recharging circuit is accessible from outside the handle for recharging.

7. A battery handle as defined in claim 5 wherein the handle includes a lamp, and a neck portion to which the head portion of the diagnostic instrument can be releasably secured, the lamp being positioned in the neck portion.

8. A battery handle as defined in claim 7 wherein the instrument head portion is secured to the handle neck portion by a threaded connection.

9. A battery handle as defined in claim 7 wherein the lamp and neck portion are arranged so that the handle can be effectively used for diagnostic purposes with or without the instrument head portion.

10. A battery handle as defined in claim 7 together with heat insulating means encircling the lamp.

* * * * *